(12) United States Patent
Burkett

(10) Patent No.: US 9,648,816 B2
(45) Date of Patent: May 16, 2017

(54) ONION VARIETY SV4522NB

(71) Applicant: SEMINIS VEGETABLE SEEDS, INC., St. Louis, MO (US)

(72) Inventor: Al Burkett, St. Louis, MO (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 155 days.

(21) Appl. No.: 14/602,103

(22) Filed: Jan. 21, 2015

(65) Prior Publication Data

US 2016/0205884 A1    Jul. 21, 2016

(51) Int. Cl.
*A01H 5/08*    (2006.01)

(52) U.S. Cl.
CPC ...................................... *A01H 5/08* (2013.01)

(58) Field of Classification Search
None
See application file for complete search history.

(56) References Cited

PUBLICATIONS

Anitha et al. (Indian Journal of Plant Protection (2011), vol. 39, Issue: 2 pp. 81-92).*
Moose SP, Mumm RH., "Molecular plant breeding as the foundation for 21st century crop improvement", *Plant Physiol.*; 147(3):969-77; Jul. 2008.
Variety spesific information as indicated in transmittal letter of Apr. 18, 2016 Information Disclosure Statement for U.S. Appl. No. 14/602,103.

* cited by examiner

*Primary Examiner* — Brent Page
*Assistant Examiner* — Jared Shapiro
(74) *Attorney, Agent, or Firm* — Dentons US LLP; Alissa Eagle Esq.

(57) ABSTRACT

The invention provides seed and plants of the onion line designated SV4522NB. The invention thus relates to the plants, seeds and tissue cultures of onion line SV4522NB, and to methods for producing an onion plant produced by crossing a plant of onion line SV4522NB with itself or with another onion plant, such as a plant of another line. The invention further relates to seeds and plants produced by such crossing. The invention further relates to parts of a plant of onion line SV4522NB, including the bulbs and gametes of such plants.

24 Claims, 2 Drawing Sheets

ONION VARIETY SV4522NB

FIELD OF THE INVENTION

The present invention relates to the field of plant breeding and, more specifically, to the development of onion line SV4522NB.

BACKGROUND OF THE INVENTION

The goal of vegetable breeding is to combine various desirable traits in a single variety/hybrid. Such desirable traits may include any trait deemed beneficial by a grower and/or consumer, including greater yield, resistance to insects or disease, tolerance to environmental stress, and nutritional value.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different genotypes produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new lines are evaluated to determine which of those have commercial potential.

One breeding technique of value for use in onions is use of "dihaploid" breeding. This technique involves doubling the chromosome number of a haploid derived from a starting heterozygous plant in order to recover a progeny dihaploid plant that is homozygous, with both sets of chromosomes being recovered from the haploid in the case of a diploid species. Polyploids may also be obtained using this method.

One crop species which has been subject to such breeding programs and is of particular value is onion. Onions belong to the lily family, Amaryllidaceae, and the genus, *Allium*. This genus comprises a group of perennial herbs having bulbous, onion-scented underground leaves, including such commonly cultivated crops as onion, garlic, chives, shallots and leeks. It also includes ornamental species grown for their flowers.

Onions are an important vegetable world-wide, ranking second among all vegetables in economic importance with an estimated value of $6 billion dollars annually. The onion is also one of the oldest cultivated vegetables. Common bulbing onions are of the species *Allium cepa*. Onions are classified in numerous ways, by basic use, flavor, color, shape of the bulb, and day length. Onions come in white, yellow, and red colors. The bulb may be rounded, flattened, or torpedo shaped.

Commercial onions include "storage onions", "fresh onions", "pearl or mini onions", and "green bunching onions." Green bunching onions, also called Welsh onions or Japanese bunching onions, are young onion plants that are harvested with the green tops attached and are used both fresh and as a cooked ingredient. They are mild in flavor and are used frequently in salads. These are typically of the species *Allium fistulosum*. Green bunching onions are available in the United States during the entire year.

Onions are most frequently grown from seed. A small fraction of the crop is grown from transplants or "sets". Onion sets are produced by sowing seed very thickly one year, resulting in small bulbs that that are easily set out and grown into mature bulbs the next year. Onion transplants are seedlings that are sown thickly and grown without bulbing for 45-90 days. These plants are then harvested and trimmed and replanted at lower populations in the final fields for bulb production. While breeding efforts to date have provided a number of useful onion lines with beneficial traits, there remains a great need in the art for new lines with further improved traits. Such plants would benefit farmers and consumers alike by improving crop yields and/or quality.

SUMMARY OF THE INVENTION

In one aspect, the present invention provides an onion plant of the onion line designated SV4522NB. Also provided are onion plants having all the physiological and morphological characteristics of onion line SV4522NB. Parts of the onion plant of the present invention are also provided, for example, including pollen, an ovule, scion, a rootstock, a bulb, and a cell of the plant.

The invention also concerns seed of onion line SV4522NB. The onion seed of the invention may be provided, in certain illustrative embodiments, as an essentially homogeneous population of onion seed of the line designated SV4522NB. Essentially homogeneous populations of seed are generally free from substantial numbers of other seed. Therefore, in one embodiment, seed of line SV4522NB may be defined as forming at least about 90% of the total seed, including at least about 91%, 92%, 93%, 94%, 95%, 96%, 97%, 98%, 99%, or more of the seed. The population of onion seed may be particularly defined as being essentially free from hybrid seed. The seed population may be separately grown to provide an essentially homogeneous population of onion plants designated SV4522NB.

In another aspect of the invention, a plant of onion line SV4522NB comprising an added heritable trait is provided. The heritable trait may comprise a genetic locus that is, for example, a dominant or recessive allele. In one embodiment of the invention, a plant of onion line SV4522NB is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of the line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

In another aspect of the invention, a tissue culture of regenerable cells of a plant of line SV4522NB is provided. The tissue culture will preferably be capable of regenerating plants capable of expressing all of the physiological and morphological characteristics of the line, and of regenerating plants having substantially the same genotype as other plants of the line. Examples of some of the physiological and morphological characteristics of the line SV4522NB include those traits set forth in the tables herein. The regenerable cells in such tissue cultures may be derived, for example, from embryos, meristems, pollen, leaves, anthers, roots, root tips, pistil, flower, seed and stalks. Still further, the present invention provides onion plants regenerated from a tissue culture of the invention, the plants having all the physiological and morphological characteristics of line SV4522NB.

In yet another aspect of the invention, processes are provided for producing onion seeds, plants and bulbs, which processes generally comprise crossing a first parent onion plant with a second parent onion plant, wherein at least one of the first or second parent onion plants is a plant of the line designated SV4522NB. These processes may be further exemplified as processes for preparing hybrid onion seed or plants, wherein a first onion plant is crossed with a second onion plant of a different, distinct line to provide a hybrid that has, as one of its parents, the onion plant line SV4522NB. In these processes, crossing will result in the production of seed. The seed production occurs regardless of whether the seed is collected or not.

In one embodiment of the invention, the first step in "crossing" comprises planting seeds of a first and second parent onion plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent onion plants into plants that bear flowers. A third step may comprise preventing self-pollination of the plants, such as by emasculating the flowers, (i.e., killing or removing pollen).

A fourth step for a hybrid cross may comprise cross-pollination between the first and second parent onion plants. Yet another step comprises harvesting the seeds from at least one of the parent onion plants. The harvested seed can be grown to produce an onion plant or hybrid onion plant.

The present invention also provides the onion seeds and plants produced by a process that comprises crossing a first parent onion plant with a second parent onion plant, wherein at least one of the first or second parent onion plants is a plant of the line designated SV4522NB. In one embodiment of the invention, onion seed and plants produced by the process are first generation (F1) hybrid onion seed and plants produced by crossing a plant in accordance with the invention with another, distinct plant. The present invention further contemplates plant parts of such an F1 hybrid onion plant, and methods of use thereof. Therefore, certain exemplary embodiments of the invention provide an F1 hybrid onion plant and seed thereof.

In still yet another aspect of the invention, the genetic complement of the onion plant line designated SV4522NB is provided. The phrase "genetic complement" is used to refer to the aggregate of nucleotide sequences, the expression of which sequences defines the phenotype of, in the present case, an onion plant, or a cell or tissue of that plant. A genetic complement thus represents the genetic makeup of a cell, tissue or plant, and a hybrid genetic complement represents the genetic make up of a hybrid cell, tissue or plant. The invention thus provides onion plant cells that have a genetic complement in accordance with the onion plant cells disclosed herein, and plants, seeds and plants containing such cells.

Plant genetic complements may be assessed by genetic marker profiles, and by the expression of phenotypic traits that are characteristic of the expression of the genetic complement, e.g., isozyme typing profiles. It is understood that line SV4522NB could be identified by any of the many well known techniques such as, for example, Simple Sequence Length Polymorphisms (SSLPs) (Williams et al., Nucleic Acids Res., 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., Science, 280:1077-1082, 1998).

In still yet another aspect, the present invention provides hybrid genetic complements, as represented by onion plant cells, tissues, plants, and seeds, formed by the combination of a haploid genetic complement of an onion plant of the invention with a haploid genetic complement of a second onion plant, preferably, another, distinct onion plant. In another aspect, the present invention provides an onion plant regenerated from a tissue culture that comprises a hybrid genetic complement of this invention.

In still yet another aspect, the invention provides a method of determining the genotype of a plant of onion line SV4522NB comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

In still yet another aspect, the present invention provides a method of producing a plant derived from line SV4522NB, the method comprising the steps of: (a) preparing a progeny plant derived from line SV4522NB, wherein said preparing comprises crossing a plant of the line SV4522NB with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from line SV4522NB. The plant derived from line SV4522NB may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from line SV4522NB is obtained which possesses some of the desirable traits of the line as well as potentially other selected traits.

In certain embodiments, the present invention provides a method of producing onion comprising: (a) obtaining a plant of onion line SV4522NB, wherein the plant has been cultivated to maturity, and (b) collecting onions from the plant.

These and other features and advantages of this invention are described in, or are apparent from, the following detailed description of various exemplary embodiments of the devices and methods according to this invention.

DETAILED DESCRIPTION OF THE INVENTION

Figure 1A:
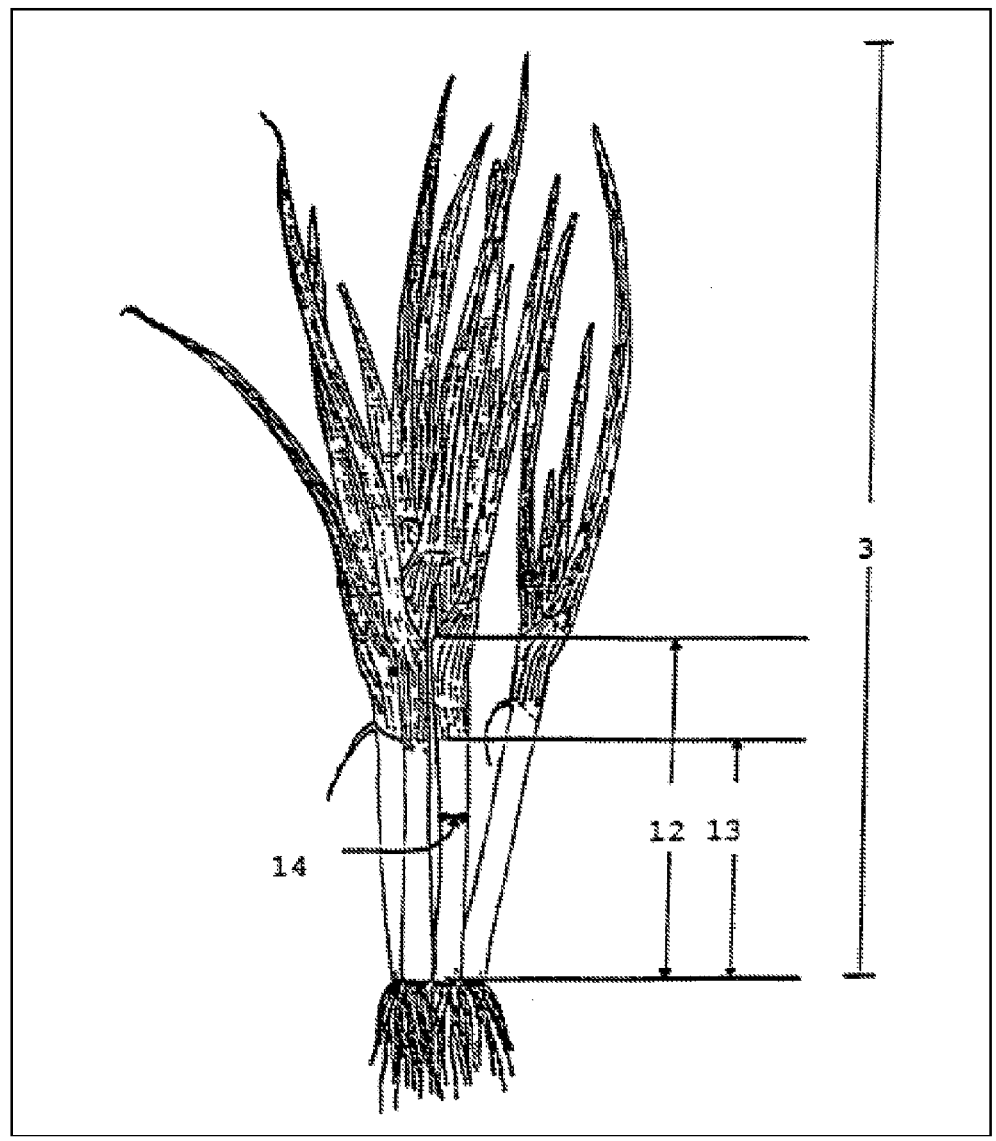
FIG. 1A: Image "A": 3. Plant height 12. Pseudostem: length 13. Pseudostem: length of blanched column 14. Pseudostem: diameter
Figure 1B:
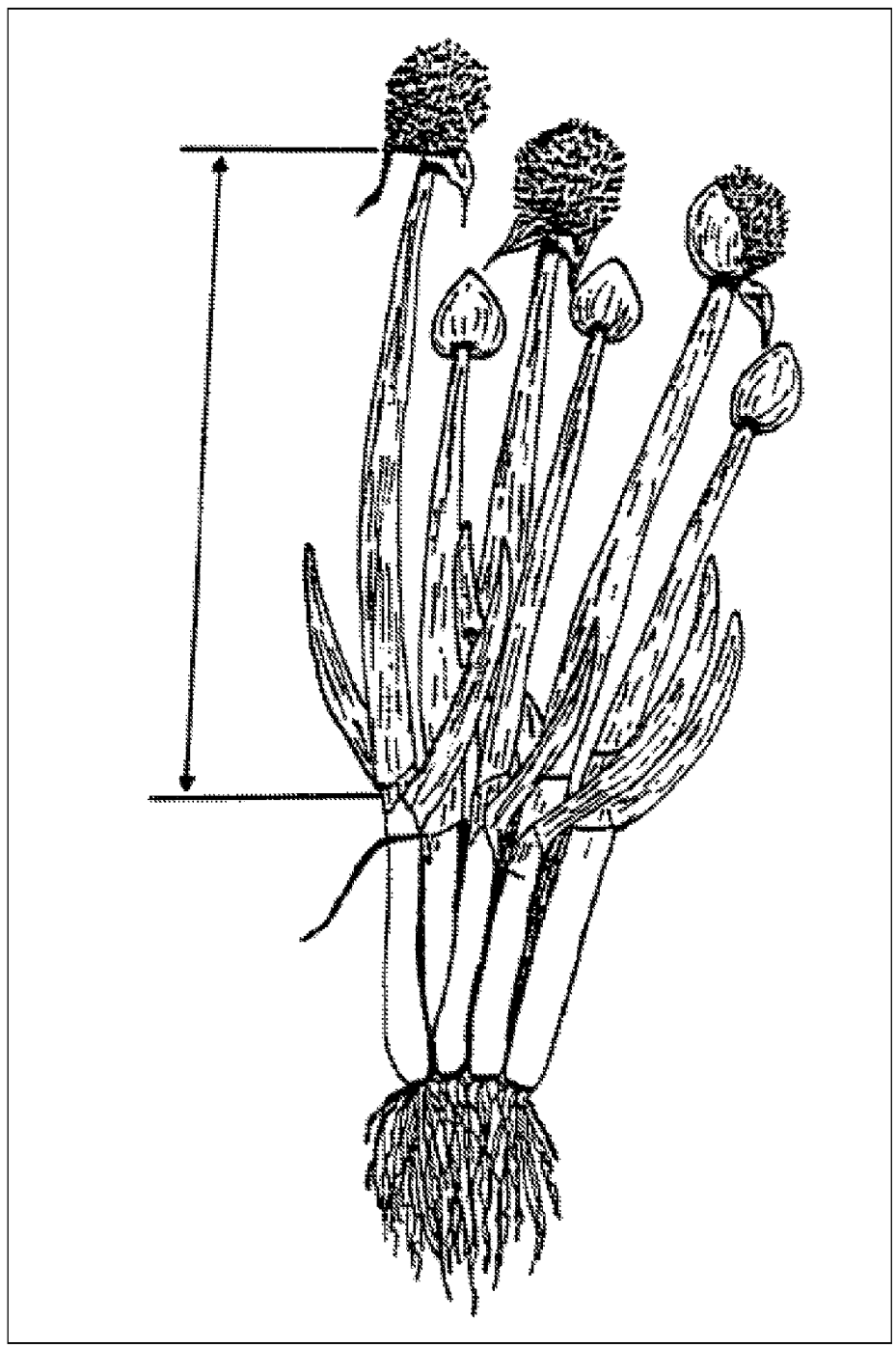
FIG. 1B: Image "B": 18. Bolting stem: scape length (in the second year)

The invention provides methods and compositions relating to plants, seeds and derivatives of the onion line designated SV4522NB. This line shows uniformity and stability within the limits of environmental influence for the traits described hereinafter. Onion line SV4522NB provides sufficient seed yield. By crossing with a distinct second plant, uniform F1 hybrid progeny can be obtained.

"Bunching Onion", *Allium cepa×Alium fistulosum* (4n) is a cool season (tolerant of frost) biennial plant. By "biennial plant" it is meant that *Allium cepa×Alium fistulosum* (4n). produces a plant in the first season and seeds in the second. Onion plants may be grown at any temperature that allows for the growth and development of the plant. Temperatures that allow for the growth and development of the onion plants of the present invention include those between about 45° F. and about 85° F. or between about 50° F. and about 80° F. Preferable temperatures for growth and development for onion plants of the present invention are between about 55° F. and about 75° F. In another aspect, temperature ranges that allow for seedling growth may be lower than those for plant growth and development. Temperatures that allow for seedling growth include those between about 58° F. and about 87° F. or between about 63° F. and about 82° F. In a preferred aspect, temperatures for seedling growth are those temperatures between about 68° F. to about 77° F.

Onion line SV4522NB is also known as "PX-07424522" or "XMN-74-2041C".

SV4522NB is uniform and stable. A small percentage of variants can occur within commercially acceptable limits for almost any characteristic during the course of repeated multiplication. However no variants are expected.

A. PHYSIOLOGICAL AND MORPHOLOGICAL CHARACTERISTICS OF ONION LINE SV4522NB

In accordance with one aspect of the present invention, there is provided a plant having the physiological and morphological characteristics of onion line SV4522NB. A description of the physiological and morphological characteristics of onion line SV4522NB is presented in Table 1.

TABLE 1

Physiological and Morphological Characteristics of Line SV4522NB

| CHARACTERISTIC | SV4522NB | Green Banner |
|---|---|---|
| Type: | bunching | bunching |
| Type: maturity (days) | early (75-90) | early |
| Plant | | |
| growth type | single pseudostem | single pseudostem |
| height (above soil line to the highest point of any foliage) (in centimeters) | 45.8 cm | Green Banner (46.3 cm) |
| height (number of centimeters taller than comparable variety) | +0.1 cm | Green Banner |
| height (number of centimeters shorter than comparable variety) | −0.1 cm | Green Banner |
| attitude | erect | erect |
| height (refer to image "A" for measurement instructions) | medium | medium |
| number of leaves per pseudostem | medium | medium |
| Foliage | | |
| attitude | erect | erect |
| waxiness | strong | medium |
| Leaf | | |
| color | medium green | medium green |
| color (RHS Color Chart Value) | 137B | 137B |
| hue of green color | absent | absent |
| intensity of green color (Only for varieties with additional hue absent) | medium | medium |
| length (before maturity yellowing begins) | 45.9 cm | 41.8 cm |
| length | medium | medium |
| width | 8.8 mm | 7.7 cm |
| diameter | medium | medium |
| thickness (at mid-length of longest leaf) (in millimeters) | 7.4 mm | 5.9 mm |
| curvature | weak | medium |
| bloom | medium | medium |
| Pseudostem | | |
| length (refer to image "A" for measurement instructions) | medium | medium |
| length of blanched column (refer to image "A" for measurement instructions) | medium | medium |
| diameter (refer to image "A" for measurement instructions) | medium | medium |
| anthocyanin coloration | absent | absent |
| Sheath | | |
| column length (height from soil line to base of lowest succulent leaf) (length in millimeters) | 12.7 mm | 10.5 mm |
| column diameter (at mid-length) (in millimeters) | 12.4 mm | 14.7 mm |
| scape: length (from soil line to base of inflorescence) (in centimeters) | 86.4 cm | 83.9 cm |
| scape: diameter (at mid-length) (in millimeters) | 26.0 mm | 18.8 mm |
| Inflorescence | | |
| Umbel (for seed production) maximum number per plant) | 1.5 | 2 |
| minimum number per plant | 1 | 1 |
| average number per plant | 1.5 | 1.4 |

TABLE 1-continued

Physiological and Morphological
Characteristics of Line SV4522NB

| CHARACTERISTIC | SV4522NB | Green Banner |
|---|---|---|
| diameter (in millimeters) | 71.5 mm | 63.9 mm |
| type | compact | compact |
| spathe | long beak | long beak |
| flower color | white | white |
| anther length (in millimeters) | 2.1 mm | 2.3 mm |
| anther color | pale yellow | pale yellow |
| pollen viability | fertile | fertile |
| sepal shape | long pointed | long pointed |
| Bulb | | |
| Pseudostem: bulbing | absent or very weak | absent or very weak |
| Tendency to bolting | absent or very weak | absent or very weak |
| bolting stem: scape length (in second year) (refer to image "B" for measurement instructions) | long | long |
| Time of flowering | medium | medium |
| Male sterility | absent | absent |

*These are typical values. Values may vary due to environment. Other values that are substantially equivalent are within the scope of the invention.

B. BREEDING ONION LINE SV4522NB

One aspect of the current invention concerns methods for crossing the onion line SV4522NB with itself or a second plant and the seeds and plants produced by such methods. These methods can be used for propagation of line SV4522NB, or can be used to produce hybrid onion seeds and the plants grown therefrom. Hybrid seeds are produced by crossing line SV4522NB with second onion parent line.

The development of new varieties using one or more starting varieties is well known in the art. In accordance with the invention, novel varieties may be created by crossing line SV4522NB followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) in progeny. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner, true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with line SV4522NB and progeny thereof to achieve a homozygous line.

New varieties may be created, for example, by crossing line SV4522NB with any second plant and selection of progeny in various generations and/or by doubled haploid technology. In choosing a second plant to cross for the purpose of developing novel lines, it may be desired to choose those plants which either themselves exhibit one or more selected desirable characteristics or which exhibit the desired characteristic(s) in progeny. After one or more lines are crossed, true-breeding lines may be developed.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The line of the present invention is particularly well suited for the development of new lines based on the elite nature of the genetic background of the line. In selecting a second plant to cross with SV4522NB for the purpose of developing novel onion lines, it will typically be preferred to choose those plants which either themselves exhibit one or more selected desirable characteristics or which exhibit the desired characteristic(s) when in hybrid combination. Examples of desirable characteristics may include, but are not necessarily limited to, enhanced flavor; reduced flavor; low pungency (such producing a bulb having a pyruvic acid development (PAD) measurement of less than 5.5 μM/g FW of pyruvate, for example); increased resistance to viral pathogens, for example, iris yellow spot virus, onion yellow dwarf virus, onion mosaic virus, and onion mite-borne latent virus; increased resistance to one or more bacterial pathogens, for example, *Erwinia carotovora* ssp. *carotovora*, *E. chrysanthemi*, *Pseudomonas gladioli*, and *Enterobacter cloacae*, such as are related to bacterial soft rot, onion bacterial blight, caused by *Xanthomonas* sp; increased resistance to one or more fungal diseases, such as purple blotch, caused by the fungus *Alternaria porri*, downy mildew, caused by the fungus *Peronospora destructor*; *Botrytis* leaf blight (Blast) symptoms, caused by *Botrytis* spp.; white rot, caused by *Fusarium*; and *Botrytis* neck rot; increased resistance to insects (e.g. bulb mites; maggots; pea leafminer; thrips; wheat curl mite; and onion eelworm); and the like.

Furthermore, examples of desirable characteristics may also include, in specific embodiments, high seed yield, high seed germination, seedling vigor, high bulb yield, disease tolerance or resistance, and adaptability for soil and climate conditions. Consumer-driven traits, such as bulb shape, color, texture, and taste are other examples of traits that may be incorporated into new lines of onion plants developed by this invention.

C. FURTHER EMBODIMENTS OF THE INVENTION

In certain aspects of the invention, plants described herein are provided modified to include at least a first desired heritable trait. Such plants may, in one embodiment, be developed by a plant breeding technique called backcrossing, wherein essentially all of the physiological and morphological characteristics of a variety are recovered in addition to a genetic locus transferred into the plant via the backcrossing technique. The term single locus converted plant as used herein refers to those onion plants which are developed by a plant breeding technique called backcrossing, wherein essentially all of the desired physiological and morphological characteristics of a variety are recovered in addition to the single locus transferred into the variety via the backcrossing technique.

Backcrossing methods can be used with the present invention to improve or introduce a characteristic into the present variety. The parental onion plant which contributes the locus for the desired characteristic is termed the nonrecurrent or donor parent. This terminology refers to the fact that the nonrecurrent parent is used one time in the backcross protocol and therefore does not recur. The parental onion plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until an onion plant is obtained wherein essentially all of the desired physiological and morphological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny onion plants of a backcross in which SV4522NB is the recurrent parent comprise (i) the desired trait from the non-recurrent parent and (ii) all of the physiological and morphological characteristics of onion line SV4522NB as determined at the 5% significance level when grown in the same environmental conditions.

Onion varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (Plant Physiology, 147: 969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. These additional loci may confer, for example, such traits as a disease resistance or a bulb quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many single locus traits have been identified that are not regularly selected for in the development of a new inbred but that can be improved by backcrossing techniques. Single locus traits may or may not be transgenic; examples of these traits include, but are not limited to, male sterility, herbicide resistance, resistance to bacterial, fungal, or viral disease, insect resistance, restoration of male fertility, modified fatty acid or carbohydrate metabolism, and altered nutritional quality. These comprise genes generally inherited through the nucleus.

Direct selection may be applied where the single locus acts as a dominant trait. For this selection process, the progeny of the initial cross are assayed for viral resistance and/or the presence of the corresponding gene prior to the backcrossing. The selection eliminates any plants that do not have the desired gene and resistance trait, and only those plants that have the trait are used in the subsequent backcross. This process is then repeated for all additional backcross generations.

Selection of onion plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection applicable to the breeding of onion are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., Nucleic Acids Res., 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., Science, 280:1077-1082, 1998).

D. PLANTS DERIVED FROM ONION LINE SV4522NB BY GENETIC ENGINEERING

Many useful traits that can be introduced by backcrossing, as well as directly into a plant, are those which are introduced by genetic transformation techniques. Genetic transformation may therefore be used to insert a selected transgene into the onion line of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, Agrobacterium-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

Many useful traits are those which are introduced by genetic transformation techniques. Methods for the genetic transformation of onion are known to those of skill in the art. For example, methods which have been described for the genetic transformation of onion may include electroporation, electrotransformation, microprojectile bombardment, Agrobacterium-mediated transformation, direct DNA uptake transformation of protoplasts and silicon carbide fiber-mediated transformation. See, e.g., Khachatourians et al., (In: Transgenic Plants and Crops, Marcel Dekker, Inc., 2002)

It is understood to those of skill in the art that a transgene need not be directly transformed into a plant, as techniques for the production of stably transformed onion plants that pass single loci to progeny by Mendelian inheritance is well known in the art. Such loci may therefore be passed from parent plant to progeny plants by standard plant breeding techniques that are well known in the art. Examples of traits that may be introduced into an onion plant according to the invention include, for example, male sterility, herbicide resistance, disease resistance, insect resistance, and enhanced nutritional quality.

PCR and Southern hybridization are two examples of molecular techniques that can be used for confirmation of the presence of a given locus and thus conversion of that locus.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target onion cells. The screen disperses the particles so that they are not delivered to the recipient cells in large aggregates. Microprojectile bombardment techniques are widely applicable, and may be used to transform virtually any plant species.

Agrobacterium-mediated transfer is another widely applicable system for introducing gene loci into plant cells. An advantage of the technique is that DNA can be introduced into whole plant tissues, thereby bypassing the need for regeneration of an intact plant from a protoplast. Modern Agrobacterium transformation vectors are capable of replication in E. coli as well as Agrobacterium, allowing for convenient manipulations (Klee et al., Bio-Technology, 3(7):637-642, 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, Agrobacterium containing both armed and disarmed Ti genes can be used for transformation.

In those plant strains where Agrobacterium-mediated transformation is efficient, it is the method of choice because of the facile and defined nature of the gene locus transfer. The use of Agrobacterium-mediated plant integrating vectors to introduce DNA into plant cells is well known in the art (Fraley et al., Bio/Technology, 3:629-635, 1985; U.S. Pat. No. 5,563,055). One example of an onion transformation protocol for Agrobacterium tumefaciens-mediated transformation involves use of immature embryos as an explant source (Eady et al., Plant Cell Rep., 19:376-381, 2000). Multiple-shoot formation from primary transgenic material made possible the clonal multiplication of transformants.

Transformation of plant protoplasts also can be achieved using methods based on calcium phosphate precipitation, polyethylene glycol treatment, electroporation, and combinations of these treatments (see, e.g., Potrykus et al., Mol. Gen. Genet., 199:183-188, 1985; Omirulleh et al., Plant Mol. Biol., 21(3):415-428, 1993; Fromm et al., Nature, 312:791-793, 1986; Uchimiya et al., Mol. Gen. Genet., 204:204, 1986; Marcotte et al., Nature, 335:454, 1988). Transformation of plants and expression of foreign genetic elements is exemplified in Choi et al. (Plant Cell Rep., 13: 344-348, 1994), and Ellul et al. (Theor. Appl. Genet., 107:462-469, 2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, e.g., Odel et al., Nature, 313:810, 1985), including in monocots (see, e.g., Dekeyser et al., Plant Cell, 2:591, 1990; Terada and Shimamoto, Mol. Gen. Genet., 220:389, 1990); a tandemly duplicated version of the CaMV 35S promoter, the enhanced 35S promoter (P-e35S) the nopaline synthase promoter (An et al., Plant Physiol., 88:547, 1988), the octopine synthase promoter (Fromm et al., Plant Cell, 1:977, 1989); and the figwort mosaic virus (P-FMV) promoter as described in U.S. Pat. No. 5,378,619 and an enhanced version of the FMV promoter (P-eFMV)

where the promoter sequence of P-FMV is duplicated in tandem, the cauliflower mosaic virus 19S promoter, a sugarcane bacilliform virus promoter, a commelina yellow mottle virus promoter, and other plant DNA virus promoters known to express in plant cells.

A variety of plant gene promoters that are regulated in response to environmental, hormonal, chemical, and/or developmental signals can also be used for expression of an operably linked gene in plant cells, including promoters regulated by (1) heat (Callis et al., Plant Physiol., 88:965, 1988), (2) light (e.g., pea rbcS-3A promoter, Kuhlemeier et al., Plant Cell, 1:471, 1989; maize rbcS promoter, Schaffner and Sheen, Plant Cell, 3:997, 1991; or chlorophyll a/b-binding protein promoter, Simpson et al., EMBO J., 4:2723, 1985), (3) hormones, such as abscisic acid (Marcotte et al., Plant Cell, 1:969, 1989), (4) wounding (e.g., wunl, Siebertz et al., Plant Cell, 1:961, 1989); or (5) chemicals such as methyl jasmonate, salicylic acid, or Safener. It may also be advantageous to employ organ-specific promoters (e.g., Roshal et al., EMBO J., 6:1155, 1987; Schernthaner et al., EMBO J., 7:1249, 1988; Bustos et al., Plant Cell, 1:839, 1989).

Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into an onion plant according to the invention. Non-limiting examples of particular genes and corresponding phenotypes one may choose to introduce into an onion plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., Biotech. Gen. Engin. Rev., 9:207, 1991). The RNA could also be a catalytic RNA molecule (i.e., a ribozyme) engineered to cleave a desired endogenous mRNA product (see for example, Gibson and Shillito, Mol. Biotech., 7:125, 1997). Thus, any gene which produces a protein or mRNA which expresses a phenotype or morphology change of interest is useful for the practice of the present invention.

E. DEFINITIONS

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Regeneration: The development of a plant from tissue culture.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Self-pollination: The transfer of pollen from the anther to the stigma of the same plant.

Single Locus Converted (Conversion) Plant: Plants which are developed by a plant breeding technique called backcrossing wherein essentially all of the physiological and morphological characteristics of an inbred are recovered in addition to the characteristics conferred by the single locus transferred into the inbred via the backcrossing technique. By "essentially all," it is meant that all of the characteristics of a plant are recovered that are otherwise present when compared in the same environment and save for the converted locus, other than an occasional variant trait that might arise during backcrossing or direct introduction of a transgene. A single locus may comprise one gene, or in the case of transgenic plants, one or more transgenes integrated into the host genome at a single site (locus).

Substantially Equivalent: A characteristic that, when compared, does not show a statistically significant difference (e.g., p=0.05) from the mean.

Tetraploid: A cell or organism having four sets of chromosomes.

Tissue Culture: A composition comprising isolated cells of the same or a different type or a collection of such cells organized into parts of a plant.

Transgene: A genetic locus comprising a sequence which has been introduced into the genome of a garden onion plant by transformation.

F. DEPOSIT INFORMATION

A deposit of onion line SV4522NB, disclosed above and recited in the claims, has been made with the American Type Culture Collection (ATCC), 10801 University Blvd., Manassas, Va. 20110-2209, USA, and assigned ATCC Accession No. PTA-121600. The seeds were deposited with the ATCC on Sep. 15, 2014. Access to this deposit will be available during the pendency of the application to the Commissioner of Patents and Trademarks and persons determined by the Commissioner to be entitled thereto upon request. The deposits will be maintained in the ATCC Depository, which is a public depository, for a period of 30 years, or 5 years after the most recent request, or for the enforceable life of the patent, whichever is longer, and will be replaced if it becomes nonviable during that period. Applicant does not waive rights granted under this patent or under the Plant Variety Protection Act (7 U.S.C. 2321 et seq.).

Although the foregoing invention has been described in detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

What is claimed is:

1. A seed of onion line SV4522NB, a sample of seed of said line having been deposited under ATCC Accession Number PTA-121600.

2. A plant grown from the seed of claim 1.

3. A plant part of the plant of claim 2.

4. The plant part of claim 3, wherein said part is selected from the group consisting of a pollen, an ovule, scion, a rootstock, a bulb, and a cell of the plant.

5. An onion plant having all the physiological and morphological characteristics of the onion plant of claim 2.

6. A tissue culture of regenerable cells of onion line SV4522NB, a sample of seed of said line having been deposited under ATCC Accession Number PTA-121600.

7. The tissue culture according to claim 6, comprising cells or protoplasts from a plant part selected from the group consisting of embryos, meristems, pollen, leaves, anthers, roots, root tips, pistil, flower, seed and stalks.

8. An onion plant regenerated from the tissue culture of claim 6, wherein the regenerated plant expresses all of the physiological and morphological characteristics of onion line SV4522NB, a sample of seed of said line having been deposited under ATCC Accession Number PTA-121600.

9. A method of producing onion seed, comprising crossing the plant of claim 2 with itself or a second onion plant.

10. The method of claim 9, wherein the plant of onion line SV4522NB is the female parent.

11. The method of claim 9, wherein the plant of onion line SV4522NB is the male parent.

12. An F1 hybrid seed produced by the method of claim 9.

13. An F1 hybrid plant produced by growing the seed of claim 12.

14. A method for producing a seed of a line SV4522NB-derived onion plant comprising the steps of:
   (a) crossing an onion plant of line SV4522NB with a second onion plant, a sample of seed of said line having been deposited under ATCC Accession Number PTA-121600; and
   (b) allowing seed of a SV4522NB-derived onion plant to form.

15. The method of claim 14, further comprising the steps of:
   (c) crossing a plant grown from said SV4522NB-derived onion seed with itself or a second onion plant to yield additional SV4522NB-derived onion seed;
   (d) growing said additional SV4522NB-derived onion seed of step (c) to yield additional SV4522NB-derived onion plants; and
   (e) repeating the crossing and growing steps of (c) and (d) to generate further SV4522NB-derived onion plants.

16. A method of vegetatively propagating a plant of onion line SV4522NB comprising the steps of:
   (a) collecting tissue capable of being propagated from a plant of onion line SV4522NB, a sample of seed of said line having been deposited under ATCC Accession Number PTA-121600;
   (b) cultivating said tissue to obtain proliferated shoots; and
   (c) rooting said proliferated shoots to obtain rooted plantlets.

17. The method of claim 16, further comprising growing plants from said rooted plantlets.

18. A method of introducing a desired trait into onion line SV4522NB comprising:
   (a) crossing a plant of line SV4522NB with a second onion plant that comprises a desired trait to produce F1 progeny, a sample of seed of said line SV4522NB having been deposited under ATCC Accession Number PTA-121600;
(b) selecting an F1 progeny that comprises the desired trait;
(c) crossing the selected F1 progeny with a plant of line SV4522NB to produce backcross progeny;
(d) selecting backcross progeny comprising the desired trait; and
(e) repeating steps (c) and (d) three or more times to produce selected fourth or higher backcross progeny that comprise the desired trait and otherwise all of the physiological and morphological characteristics of onion line SV4522NB when grown in the same environmental conditions.

19. An onion plant produced by the method of claim 18.

20. A seed that produced the plant of claim 19.

21. A method of producing a plant of onion line SV4522NB comprising an added desired trait, the method comprising introducing a transgene conferring the desired trait into a plant of onion line SV4522NB, a sample of seed of said line SV4522NB having been deposited under ATCC Accession Number PTA-121600, where said plant of onion line SV4522NB comprising the added desired trait and otherwise has all of the physiological and morphological characteristics of onion line SV4522NB when grown in the same environmental conditions.

22. A plant produced by the method of claim 21.

23. A seed that produces the plant of claim 22.

24. A method of producing onions comprising:
(a) obtaining the plant of claim 2, Wherein the plant has been cultivated to maturity, and
(b) collecting at least one onion from the plant.

* * * * *